United States Patent [19]
Domagala et al.

[11] Patent Number: 5,510,375
[45] Date of Patent: Apr. 23, 1996

[54] COUMARIN DERIVATIVES AS PROTEASE INHIBITORS AND ANTIVIRAL AGENTS

[75] Inventors: John M. Domagala, Canton; Susan E. Hagen, Canton Township; Elizabeth Lunney, Ann Arbor; Bradley D. Tait, Canton, all of Mich.

[73] Assignee: Warner-Lambert Company, Morris Plains, N.J.

[21] Appl. No.: 155,728

[22] Filed: Nov. 19, 1993

[51] Int. Cl.$^6$ ............................................. A61K 31/35
[52] U.S. Cl. .................................... 514/457; 549/285
[58] Field of Search ........................... 549/285; 514/457

[56] References Cited

U.S. PATENT DOCUMENTS

| | | | |
|---|---|---|---|
| 3,810,922 | 5/1974 | Dunbar | 260/343.2 |
| 5,179,107 | 1/1993 | Afonso et al. | 514/312 |

FOREIGN PATENT DOCUMENTS

| | | |
|---|---|---|
| 3-227923 | 10/1991 | Japan . |
| 89/07939 | 9/1989 | WIPO . |
| 91/04663 | 4/1991 | WIPO . |
| 92/04326 | 3/1992 | WIPO . |
| 92/04328 | 3/1992 | WIPO . |
| 92/06687 | 4/1992 | WIPO . |
| 92/18123 | 10/1992 | WIPO . |
| 92/04327 | 3/1993 | WIPO . |
| 9418188 | 8/1994 | WIPO . |

OTHER PUBLICATIONS

T. Robins et al., *J of Acquired Immune Deficiency Syndromes*, 1993, 6:162–170.
C. Debouck, et al., *Drug Development Research*, 1990, 21:1–17.
L. H. Pearl, et al., *Nature*, 1987, 329:351–354.
J. R. Huff, *J Med Chem*, 1991, 34(8):2305–2314.
R. C. Gallo, et al., *Scientific American*, 1988, 259(4):41–48.
J. Leis, et al., *ASM News*, 1990, 56(2):77–81.
B. Zhao, et al., *Biochemistry*, 1993, 32:13054–13060.
K. Appelt, *Perspectives in Drug Discovery*, 1993, 1:23–48.
L. H. Phylip, *Biochem & Biophys Res Communications*, 1990, 171(1):439–444.
S. Galpin, et al., *Antiviral Chemistry & Chemotherapy*, 1994, 5(1):43–45.
N. E. Kohl, et al., *Proc Natl Acad Sci, USA*, 1988, 85:4686–4690.
C–F. Perno, et al., *J Infectious Diseases*, 1993, 168:1148–56.
D. J. Kempf, et al., *J Med Chem*, 1990, 33(10):2687–2689.
H. Mitsuya, *J Enz Inhib*, 1992, 6:1–8.
*Antiviral Agents Bulletin*, 1993, 6(6):163.
*Antiviral Agents Bulletin*, 1994, 7(3):69–70.
D. Richman, "Control of Virus Diseases," *45th Symposium of the Society for General Microbiology*, 1990, 261–313.
H. Toh, et al., *Nature*, 1985, 315:691.
J. Kay, et al., *Biochim. Biophys. Acta* 1: 1990, 1048.
C. Cameron, et al., *J. Biological Chem.* 168, 1993, 11711–72.
M. Graves, *Structure and Function of the Aspartic Proteases* 1991, 395–405.
C. Peng, et al., *J. Virol.*, 63: 1989, 2550–2556.
N. Kohl, et al., *Proc. Nat. Acad. Sci. USA*, 85:1988, 4689–90.
J. C. Craig, et al, *Antiviral Research*, 16:1991, 295–305.
A. G. Tomasselli, et al., *Chimica Oggi*, 9:1991, 6–27.
T. Meek, *J. Enzyme Inhibition*, 6: 1992, 65–98.
R. Nagorny, et al, *AIDS*, 7:1993, 129–130.
D. P. Fairlie, et al., *Biochem. Biophys. Res. Comm.*, 188: 1992, 631–637.

*Primary Examiner*—C. Warren Ivy
*Assistant Examiner*—Amelia Owens
*Attorney, Agent, or Firm*—Elizabeth M. Anderson

[57] ABSTRACT

The present invention relates to novel coumarin derivatives and related compounds which potently inhibit the HIV aspartyl protease blocking HIV infectivity. The coumarin derivatives are useful in the development of therapies for the treatment of viral infections and diseases, including AIDS. The present invention is also directed to methods of synthesis of multifunctionalized coumarins and of related structures.

8 Claims, No Drawings

COUMARIN DERIVATIVES AS PROTEASE INHIBITORS AND ANTIVIRAL AGENTS

1. FIELD OF THE INVENTION

The present invention relates to coumarin derivatives that are inhibitors of aspartyl proteases, in particular the aspartyl proteases found in retroviruses including Human Immunodeficiency Virus (HIV). The coumarins are expected to have utility as antiviral agents, for the treatment of infections caused by HIV or other retroviruses employing aspartyl proteases, and to be useful in the treatment of diseases caused by the retroviruses, including AIDS.

2. BACKGROUND OF THE INVENTION

Acquired Immunodeficiency Syndrome (AIDS) was coined in 1982 to describe the clinical manifestations of immunodeficiency. The etiological agent of AIDS was later associated with a retrovirus, Human Immunodeficiency Virus (HIV), from the lentivirus subfamily. At least two infectious strains of HIV have been identified, HIV-1 and HIV-2. Here, HIV will be used as a general term describing all strains and mutants of the Human Immunodeficiency Virus. The detailed study of HIV has given rise to many approaches to antiviral drug development including inhibition of the viral aspartyl protease (D. Richman, *Control of Virus Diseases*, 45th Symposium of the Society for General Microbiology, 261–313 (1990)).

Aspartyl proteases have been found in many retroviruses including the Feline Immunodeficiency Virus (FIV), the Myeloblastosis Associated Virus (MAV), HIV, and the Rous Sarcoma Virus (RSV) [H. Toh et al. *Nature*, 315: 691 (1985); J. Kay, B. M. Dunn, *Biochim. Biophys. Acta*, 1: 1048 (1990); C. Cameron, *J. Biological Chem.*, 168: 11711–720 (1993)]. Since there are structural similarities among the known retroviral proteases, compounds which inhibit the HIV protease may well inhibit other retroviral proteases.

HIV aspartyl protease is responsible for post-translational processing of viral precursor polyproteins such as pol and gag. (M. Graves, *Structure and Function of the Aspartic Proteases*, 395–405 (1991)). Cleavage of these polyproteins by this protease is essential for maturation of the virus, since the proteolytic activity necessary for polyprotein processing cannot be provided by host cellular enzymes. An important finding has been that viruses which lack this protease, or contain mutations which produce defective proteases, lack infectivity [C. Peng et al., *J. Virol.*, 63: 2550–2556 (1989) and K. Kohl et al., *Proc. Natl. Acad. Sci. USA*, 85: 4686–9 (1987)]. Thus, a selective HIV protease inhibitor has been shown to inhibit viral spread and the production of cytopathic effects in cultures of acutely infected cells (J. C. Craig, et al., *Antiviral Research*, 16: 295–305 (1991)). For this reason, inhibition of HIV protease is believed to be a viable approach to antiviral therapy.

HIV protease inhibitors have been extensively reviewed (see for example A. Tomasselli et al., *Chimica Oggi*, 9: 6–27 (1991) and T. Meek, *J. Enzyme Inhibition*, 6: 65–98 (1992)). However, the majority of these inhibitors are peptides and thus unsuitable as drugs, due to the well known pharmacological deficiencies exhibited by most peptide drugs (biliary excretion, low-bioavailability and stability in physiological milieu, etc.) Nonpeptidic inhibitors of HIV protease are thus very important, since these may lead to very useful therapeutic agents.

Coumarins containing a 4-methyl or -phenyl substituent were claimed as anticancer agents in JP 92075911-B, and 4-hydroxy coumarins (shown below), with sulfur-containing alkyl and substituted phenyl substituents at the 3-position, were active as plant growth stunting and antimicrobial agents, according to U.S. Pat. No. 3,810,922.

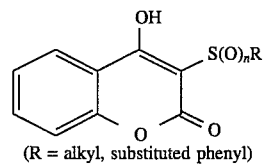

(R = alkyl, substituted phenyl)

World Patents 92/04326, WO 92/04327, WO 92/04328, and U.S. Pat. No. 5,179,107 claim quinolinones and certain coumarins with activity against DNA viruses, such as Herpes Simplex Virus (HSV), Epstein-Barr Virus (EBV), and Cytomegalovirus (CMV).

World Patent 91/04663 reports the use of 6-amino- 1,2-benzopyrone derivatives in the treatment of diseases caused by viruses, such as HIV, HSV and CMV, but only one compound was actually tested. The postulated mechanism of action involves oxidation of the amine to the 6-nitroso derivative which proceeds to oxidize a thiol side chain in the zinc finger of adenosine diphosphoribose transferase (ADPRT) causing ejection of complexed zinc. Thus the 6-amino group was the essential feature of those agents.

World Patent 92/06687 claims the use of 5-iodo-6-amino-1,2-benzopyrones as cytostatic and antiviral agents in mammalian hosts with activity against herpes and HIV viruses. The mechanism of action of these compounds may be related to ADPRT processing. Nevertheless, no satisfactory mechanism of action was proposed.

6-Aminobenzopyrones, 5-iodo-6-aminobenzopyrones, Coumarins, isoquinolines, and quinizarines were claimed as antivirals in WO 92/18123; however, only 6-amino-benzopyrone and 5-iodo-6-aminobenzopyrone were tested. These compounds are postulated to inhibit adenosine diphoshoribosyl transferase thus stopping the retroviral reverse transcriptase.

Hei 3-227923 claimed coumarins with anti-HIV activity. However, only 4-hydroxycoumarin was specifically described without discussion of a mechanism of action.

World Patent 89/07939 claimed eight coumarin derivatives as HIV reverse transcriptase inhibitors with potential antiviral activity. These derivatives are hexachlorocoumarin, 7-acetoxycoumarin, and the structures shown below.

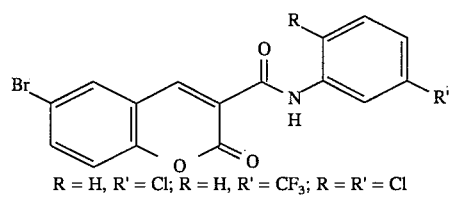

R = H, R' = Cl; R = H, R' = CF$_3$; R = R' = Cl

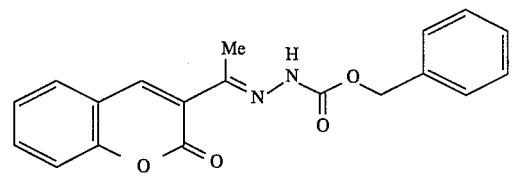

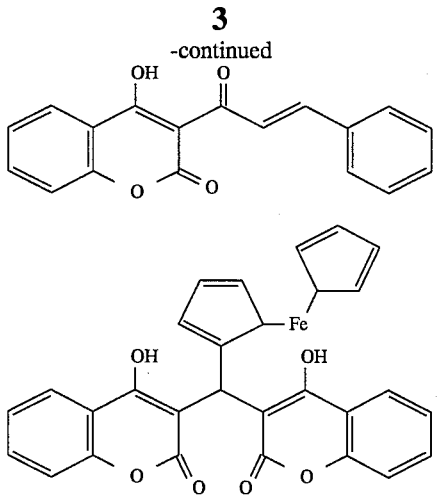

Warfarin (3-(α-acetonylbenzyl)4-hydroxycoumarin) shown below, was reported by R. Nagorny et al. in *AIDS*, 7: 129–130 (1993) as inhibiting cell-free and cell-mediated HIV infection. However, Warfarin was the only coumarin studied and its potential involvement in HIV inhibition was not specified.

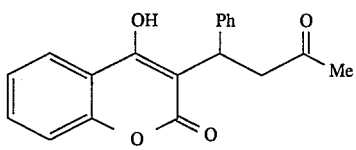

Selected flavones, structurally different from the coumarins of the present invention, were reported by Fairli et al. (*Biochem. Biophys. Res. Comm.*, 188: 631–637 (1992)) to be inhibitors of the HIV-1 protease. These compounds are shown below.

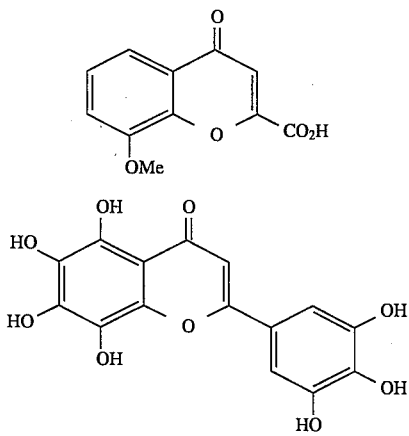

3. SUMMARY OF THE INVENTION

The present invention is based in great part on the extraordinary discovery of the inventors that novel coumarin derivatives and related compounds, selected from a very broad spectrum of tailored molecular structures, potently inhibit the HIV aspartyl protease blocking infection by HIV. The present invention is also based on the insights of the inventors regarding the mechanism of action of antiviral drugs, especially as revealed by their studies on structure-activity relationships characteristic of anti-HIV compounds that include coumarin derivatives.

The invented coumarins are expected to be extremely useful in the development of treatments for infections caused by viruses, especially by retroviruses that rely on aspartyl protease activities for replication and infectivity. One such retrovirus is HIV. As virus blockers, the coumarins are also expected to be very useful in the treatment of diseases and syndromes associated with viral pathogens. One such syndrome is AIDS.

Efficient synthesis of the biologically active coumarins, involving either de novo assemblies of the coumarin nucleus or modifications of suitably functionalized coumarins, are disclosed. Furthermore, many working examples outlining the preparation of specific coumarins whose structures contain the desired functional groups in proper geometric arrangements are given.

The testing of specific coumarins as inhibitors of the HIV aspartyl protease, based on a study of the hydrolysis of an undecapeptide enzyme substrate, and the testing of the coumarins as inhibitors of viral growth and infectivity, based on a study of infection of H9 cell lines by the HIV-1$_{iiib}$ strain, are also disclosed. Striking enzyme inhibitions, at nanomolar levels, with corresponding anti-HIV activities, were observed.

The present inventors contemplate the preparation of pharmaceutically useful antiviral compositions comprising one or more of the invented coumarins and related compounds and a pharmaceutically acceptably carrier. They also contemplate the use of these compositions, alone or in combination with other antiviral treatments, in the treatment of infections and diseases caused by retroviruses, including AIDS.

The present invention relates to compounds or the pharmaceutically acceptable salts thereof of formula

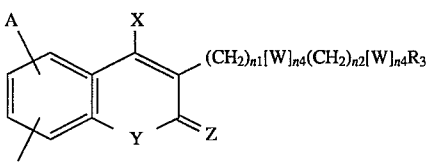

wherein

X is $OR_1$ or SH wherein $R_1$ is hydrogen or $COR_2$ wherein $R_2$ is a straight or branched alkyl chain containing 1 to 5 carbon atoms, a cyclic alkyl containing 3 to 6 carbon atoms, or a hydrogen atom;

Z is oxygen or sulfur;

Y is oxygen or sulfur;

W is oxygen, $NR_3$, $C(R_3)_2$, $NCOV_{n4}R_3$, $NR_3COV_{n4}$, CO, CH=CH, $S(O)_{n3}$, C≡C, $CNOR_4$, or $CR_3OR_3$ wherein V is oxygen, sulfur, $NR_3$, or $CHR_3$; $R_3$ is hydrogen, $(CH_2)_{n3}R_4$, or $(CH_2)_{n3}Ar$ wherein Ar is phenyl, naphthyl, or a 5- or 6-membered heterocyclic ring containing from 1 to 3 heteroatoms, a fused ring system consisting of 8–10 atoms, or a substituted derivative thereof wherein the substituents are one or more of F, Cl, Br, $OR_4$, $N(R_4)_2$, $NO_2$, $CO_2R_4$, $CON(R_4)_2$, $COR_4$, $R_4$, $OCH_2O$, $OCH_2CHO_2O$, or CN; $R_4$ is hydrogen, a straight or branched alkyl group consisting of 1 to 5 carbon atoms, a cycloalkyl consisting of 3 to 6 carbon atoms, or a substituted derivative thereof wherein the substituents are one or more of $CO_2R_2$, $CON(R_2)_2$, F, $OR_2$, phenyl, naphthyl, or $CF_3$;

n1, n2, n3, and n4 are integers of from 0 to 4, 0 to 4, 0 to 2, and 0 to 1, respectively, with the proviso that n2 is zero when intra-chain n4 is zero, and with the further proviso that n2 is of from two to four when two intra-chain groups W are heteroatoms; and A and B are independently F, Cl, Br, $OR_4$, $N(R_4)_2$, $NO_2$, $CO_2R_4$, $CON(R_4)_2$, $COR_4$, $R_4$, $OCH_2O$, $OCH_2CH_2O$, or CN.

Preferred compounds of the instant invention are those of Formula 1 above wherein X is $OR_1$ wherein $R_1$ is H or $COR_2$ wherein $R_2$ is methyl, ethyl, isopropyl, or isobutyl;

Z is oxygen;

Y is oxygen or sulfur;

W is O, $NR_3$, $C(R_3)_2$, CH=CH, or S wherein $R_3$ is H, $(CH_2)_{n3}R_4$, or $(CH_2)_{n3}Ar$ wherein Ar is phenyl, a 5- or 6-membered heterocyclic ring containing one or two heteroatoms, or a substituted derivative thereof wherein the substituents are one or more of F, Cl, Br, $OR_4$, $N(R_4)_2$, $CO_2R_4$, $R_4$, $OCH_2O$, or CN wherein $R_4$ is H, $CH_3$, $CH_3CH_2$, phenyl, or a 3- to 6-membered cycloalkyl group, or a substituted derivative thereof wherein the substituents are one or more of $CF_3$, $CO_2R_2$, $OR_2$, phenyl, or $CON(R_2)_2$;

n1, n2, n3, and n4 are integers of from 0 to 4, 0 to 4, 0 to 3, and zero or one, respectively; and A and B are independently H, C, Br, F, I, phenyl, $OR_4$, $R_4$, $CO_{2R4}$, $OCH_2O$, or $OCH_2CH_2O$.

More preferred compounds of the instant invention are those of Formula 1 above wherein X is hydroxyl;

Z is oxygen;

Y is oxygen;

W is oxygen, sulfur, or $C(R_3)_2$ wherein $R_3$ is H, $(CH_2)_{n3}R_4$, or $(CH_2)_{n3}Ar$ wherein Ar is phenyl, 2- or 3-furyl, 2-, 3-, or 4-pyridyl, or a substituted derivative thereof wherein the substituents are one or more of F, Cl, Br, $OR_4$, $CO_2R_4$, $R_4$, or $CO_2H$ wherein $R_4$ is H, methyl, ethyl, phenyl, cycloalkyl of 3 to 6 carbons, or the substituted derivatives thereof wherein the substituents are one or more of $CF_3$, $CO_2H$, $CO_2CH_3$, $CO_2CH_2CH_3$, OH, CN, or $OCH_3$;

n1, n2, n3, and n4 are integers of from 0 to 4, 0 to 2, 0 to 2, and 0 to 1, respectively; and A and B are independently chlorine, bromine, fluorine, iodine, phenyl, $OCH_3$, $CO_2CH_3$, $CO_2CH_2CH_3$, methyl, ethyl, OH or benzyl.

Most preferred compounds of the instant invention are the following:

4-Hydroxy-3-[3-3-(hydroxymethylphenoxy]propyl]-2H-1-benzopyran-2-one;

4-Hydroxy-3-[3-(3-nitrophenoxy)propyl]-2H-1-benzopyran-2-one;

4-Hydroxy-3-[2-(phenylmethoxy)ethyl]-2H-1-benzopyran-2-one;

3-[3-(3-Aminophenoxy)propyl]-4-hydroxy-2H-1-benzopyran-2-one;

6-Bromo-4-hydroxy-3-[4-(2-methoxyphenyl)butyl]-2H-1-benzopyran-2-one;

3-[3-(Cyclohexyloxy)propyl]-4-hydroxy-2H-1-benzopyran-2-one;

4-Hydroxy-3-[(phenylmethyl)thio]-2H-1-benzopyran-2-one;

4-Hydroxy-3-[(3-phenylpropyl)thio]-2H-1-benzopyran-2-one;

4-Hydroxy-3-[4-(2-methoxyphenyl)butyl]-2H-1-benzopyran-2-one;

4-Hydroxy-3-[(2-phenoxyethyl)thio]-2H-1-benzopyran-2-one;

4-Hydroxy-3-[4-(2-hydroxyphenyl)butyl]-2H-1-benzopyran-2-one;

3-[3-(4-Fluorophenoxy)propyl]-4-hydroxy-2H-1-benzopyran-2-one;

4-Hydroxy-3-[3-(4-methoxyphenoxy)propyl]-2H-1-benzopyran-2-one;

3-[3-(3-Chlorophenoxy)propyl]-4-hydroxy-2H-1-benzopyran-2-one;

4-Hydroxy-7-methoxy-3-[4-(2-methoxyphenyl)butyl]-2H-1-benzopyran-2-one;

4-Hydroxy-3-[4-(2-methoxyphenyl)butyl]-8-methyl-2H-1-benzopyran-2-one;

4-Hydroxy-3-[3-(phenylthio)propyl]-2H-1-benzopyran-2-one;

4-Hydroxy-7-methoxy-3-(3-phenoxypentyl)-2H-1-benzopyran-2-one;

4-Hydroxy-3-(3-phenoxypropyl)-6-(phenylmethyl)-2H-1-benzopyran-2-one;

3-(3,4-Dimethoxybenzyl)-4-hydroxy-8-methyl-2H-1-benzopyran-2-one;

3-[2-(Acetyl)-2-methoxyphenethyl])-4-hydroxy-2H-1-benzopyran-2-one;

4-Hydroxy-3-[3-[(tetrahydro-3-furanyl)oxy]propyl]-2H-1-benzopyran-1-one;

4-Hydroxy-[3-phenoxy-1-(phenylmethyl)propyl]-2H-1-benzopyran-2-one;

4-Hydroxy-3-[3-methyl-1-(2-phenoxyethyl)butyl]-2H-1-benzopyran-2-one;

4-Hydroxy-3-(3-phenoxy-4-phenylbutyl)-2H-1-benzopyran-2-one;

4-Hydroxy-3-(5-methyl-3-phenoxyhexyl)-2H-1-benzopyran-2-one;

4-Hydroxy-3-[4-(2-methoxyphenyl)-5-phenylpentyl]-2H-1-benzopyran-2-one;

4-Hydroxy-3-[3-(4-pyridinyloxy)propyl]-2H-1-benzopyran-2-one;

4-Hydroxy-3-[2-(phenoxymethyl)-3-phenylpropyl]-2H-1-benzopyran-2-one;

3-[3-(4,5-Dihydroxy-2-oxo-2H-benzopyran-3-yl)propoxy] benzoic acid

3-[3-(6,7-Difluoro-4-hydroxy-2-oxo-2H-1-benzopyran-3-yl)2-propenyl]oxy]benzoic Acid 3-[2-(2-Furanylmethoxy)ethyl]-4-hydroxy-2H-1-benzopyran-2-one;

4-Hydroxy-3-[3-[phenyl(phenylmethyl)amino]-propyl]-2H-1-benzopyran-2-one;

3-[(3,4-Diphenylbutyl)thio]-4-hydroxy-2H-1-benzopyran-2-one;

4-Hydroxy-3-[2-phenyl-1-(phenylmethyl)thio]ethyl]-2H-1-benzopyran-2-one;

4-Hydroxy-3-(6-methyl-3-phenoxyheptyl)-2H-1-benzopyran-2-one;

4-Hydroxy-3-[6-methyl-3-(phenoxymethyl)heptyl]-2H-1-benzopyran-2-one;

2-[3-(4-Hydroxy-2-oxo-2H-benzopyran-3-yl)propoxy]-benzenepropanoic acid

4-Hydroxy-3-[3-(2-pyridinyloxy)propyl]-2H-1-benzopyran-2-one;

4-Hydroxy-3-[3-[2-(3-phenylpropyl)phenoxy]propyl]-2H-1-benzopyran-2-one;

[[4-Hydroxy-2-oxo-3-(6-methyl-3-phenoxyheptyl)-2H-benzopyran-6-yl]oxy]acetic acid;

[[4-Hydroxy-2-oxo-3-[6-methyl-3-(phenoxymethyl)heptyl]-2H-benzopyran-6-yl]oxy]acetic acid;

4-Hydroxy-3-(3-phenoxypropyl)-2H-1-benzopyran-2-one;

[[4-Hydroxy-2-oxo-3-[3-(2-pyridinyloxy)propyl]-2H-benzopyran-6-yl]oxy]acetic acid;

[[4-Hydroxy-2-oxo-3-[3-[2-(3-phenylpropyl)-phenoxy]propyl]-2H-benzopyran-6-yl]oxy]acetic acid;
[[4-Hydroxy-3-[6-methyl-3-(phenoxymethyl)heptyl]-2-oxo-2H-benzopyran-7-yl]oxy]acetic acid;
[[4-Hydroxy-3-(6-methyl-3-phenoxyheptyl)-2-oxo-2H-benzopyran-7-yl]oxy]acetic acid;
[[4-Hydroxy-2-oxo-3-[3-(2-pyridinyloxy)propyl]-2H-benzopyran-7-yl]oxy]acetic acid;
[[4-Hydroxy-2-oxo-3-[3-[2-(3-phenylpropyl)-phenoxy]propyl]-2H-benzopyran-7-yl]oxy]acetic acid;
4-Hydroxy-6-(2-hydroxyethyl)-3-(6-methyl-3-phenoxyheptyl)-2H-1-benzopyran-2-one;
4-Hydroxy-6-(2-hydroxyethyl)-3-[6-methyl-3-(phenoxymethyl)heptyl]-2H-1-benzopyran-2-one;
2-[3-[4-Hydroxy-6-(2-hydroxyethyl)-2-oxo-2H-benzopyran-3-yl]propoxy]benzenepropanoic acid;
4-Hydroxy-6-(2-hydroxyethyl)-3-[3-(2-pyridinyloxy)propyl]-2H-1-benzopyran-2-one;
4-Hydroxy-6-(2-hydroxyethyl)-3-[3-[2-(3-phenylpropyl)phenoxy]propyl]-2H-1-benzopyran-2-one;
4-Hydroxy-7-(2-hydroxyethyl)-3-(6-methyl-3-phenoxyheptyl)-2H-1-benzopyran-2-one;
4-Hydroxy-7-(2-hydroxyethyl)-3-[6-methyl-3-phenoxymethyl)heptyl]-2H-1-benzopyran-2-one;
2-[3-[4-Hydroxy-7-(2-hydroxyethyl)-2-oxo-2H-benzopyran-3-yl]propoxy]benzenepropanoic acid;
4-Hydroxy-7-(2-hydroxyethyl)-3-[3-(2-pyridinyloxy)propyl]-2H-1-benzopyran-2-one;
4-Hydroxy-7-(2-hydroxyethyl)-3-[3-[2-(3-phenylpropyl)phenoxy]propyl]-2H-1-benzopyran-2-one;
Ethyl 3-[3-(4-hydroxy-2-oxo-2H-1-benzopyran-3-yl)propoxy]benzoate;
3-[3-(4-Hydroxy-2-oxo-2H-1-benzopyran-3-yl)propoxy]benzoic acid;
3-(4-Cyclohexylbutyl)-4-hydroxy-2H-1-benzopyran-2-one;
4-Hydroxy-3-[3-(phenylmethoxy)propyl]-2H-1-benzopyran-2-one;
3-[3-(3-Cyanophenoxy)propyl]-4-hydroxy-2H-1-benzopyran-2-one;
3-[3-(4-Hydroxy-2-oxo-2H-1-benzopyran-3-yl)propoxy]benzamide;
4,7-Dihydroxy-3-[4-(2-methoxyphenyl)butyl]-2H-1-benzopyran-2-one; and
3-[(Cyclohexylthio)phenylmethyl]-4-hydroxy-2H-1-benzopyran-2-one.

4. DETAILED DESCRIPTION OF THE INVENTION

Here, the term "alkyl" usually represented by an "R", means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl group may contain one or more sites of unsaturation such as double or triple carbon-carbon bonds. The alkyl group is unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NH—, —$CO_2$R, —COR, aryl, or heteroaryl wherein alkyl (R), aryl, and heteroaryl are defined as herein.

The term "cycloalkyl", also represented by an "R", means a saturated hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain a single double bond. The cycloalkyl ring may be unsubstituted or substituted by from 1 to 3 substituents selected alkyl, alkoxy, thioalkoxy all as defined herein, hydroxy, thiol, nitro, halogen, amino, formyl, carboxyl, nitrile, —NH—CO—R, —CO—NHR—, —$CO_2$R, —COR, aryl, or heteroaryl wherein alkyl (R), aryl, and heteroaryl are defined as herein.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 3 substituents selected from alkyl as defined above, alkoxy as defined above, thioalkoxy as defined above, hydroxy, thiol, nitro, halogen, amino, formyl, carboxy, nitrile, —NHCOR, —CONHR, —$CO_2$R, —COR, aryl, or heteroaryl wherein alkyl (R), aryl, and heteroaryl are defined as above.

The terms "heteroaryl" and "heterocycle", usually represented by an "Ar", mean a heteroaromatic radical, including a radical consisting of fused rings, which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5- 1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, thiophenyl, pyrolidinyl, piperdinyl, piperazinyl, morpholinyl, thiomorpholinyl, tetrahydrofuranyl, indanyl, benzofuranyl, benzothiophenyl, benzisoxazolyl, coumarinyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino, carboxyl, nitrile, —NHCOR, —$CO_2$R, —COR, wherein alkyl in as defined above or phenyl.

"Halogen" is fluorine, chlorine, bromine or iodine.

Some of the compounds of Formula 1 are capable of further forming pharmaceutically acceptable acid-addition and/or base salts. All of these forms are within the scope of the present invention.

Pharmaceutically acceptable acid addition salts of the compounds of Formula 1 include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science*, 66: 1–19 (1977).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science,* 66: 1–19 (1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

4.1. General Synthetic Approaches to Coumarin Derivatives

Scheme I below illustrates a general synthesis of substituted 4-hydroxy-2H-1-benzopyran-2-ones.

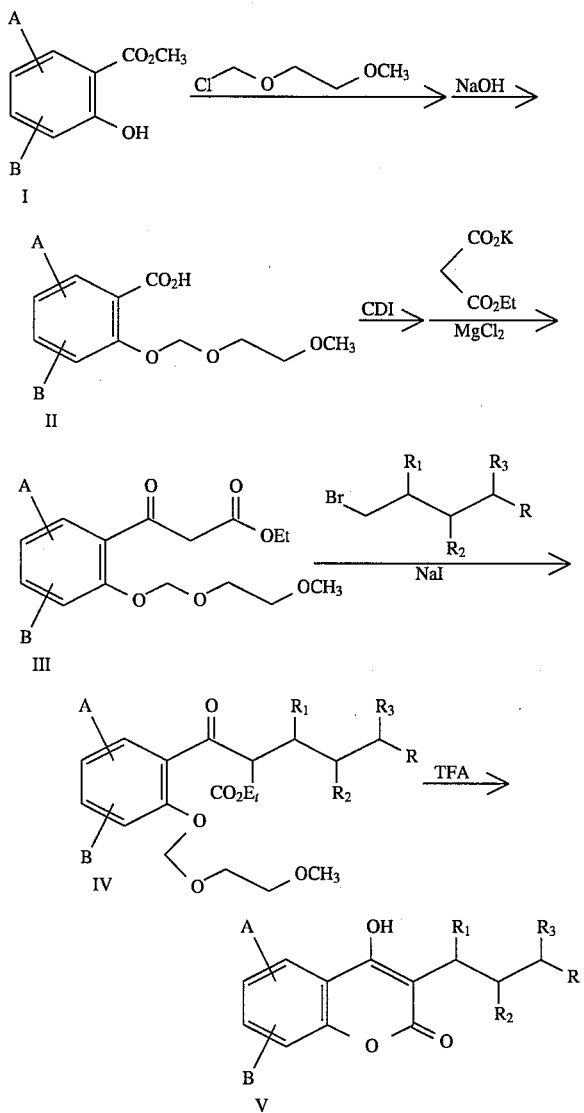

A suitably substituted methyl salicylate I is derivatized with a protecting group stable to base, e.g. methoxyethoxymethyl (MEM), and subjected to basic hydrolysis, e.g. using dilute sodium hydroxide at 0° C. to 50° C. for 3 to 18 hours, producing benzoic acid II after acidification. Benzoic acid II is activated to the imidazolide, by reaction with carbonyldiimidazole in an inert solvent such as THF at 0° C. to 40° C., which is then treated with ethyl potassium malonate and magnesium chloride in a suitable solvent, e.g. THF at 25°–70° C. for 4 to 24 hours, producing ketoester III. The ketoester is treated with a suitable base, such as sodium ethoxide or sodium hydride, in a suitable solvent, e.g. ethanol, at room temperature, and the resulting anion is alkylated with an alkyl halide, e.g. the bromide or iodide, at 25° to 80° C. for 6 to 48 hours, yielding adduct IV. Deprotection and cyclization of IV yields coumarin V. Both processes may be effected in a single step, by acid treatment, e.g. with trifluoracetic or methanesulfonic acid, in a suitable solvent, e.g. dichloromethane.

For purposes of the above and other syntheses of the compounds of the present invention, reactive functional groups present in starting materials, reaction intermediates, or reaction products may be protected during chemical reactions using protecting groups which render the reactive functional groups substantially inert to the reaction conditions. (See for example, *Protective Groups in Organic Synthesis,* 2 ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl, may all be utilized. The protecting groups may be removed, after completion of the synthetic reaction of interest, by procedures known to those skilled in the art. For example, the BOC group may be removed by acidolysis, the trityl group by hydrogenolysis, TBDMS by treatment with fluoride ions, and TCEC by treatment with zinc.

Scheme II illustrates an alternative approach to 4-hydroxy-2-benzopyran-2-ones.

SCHEME II

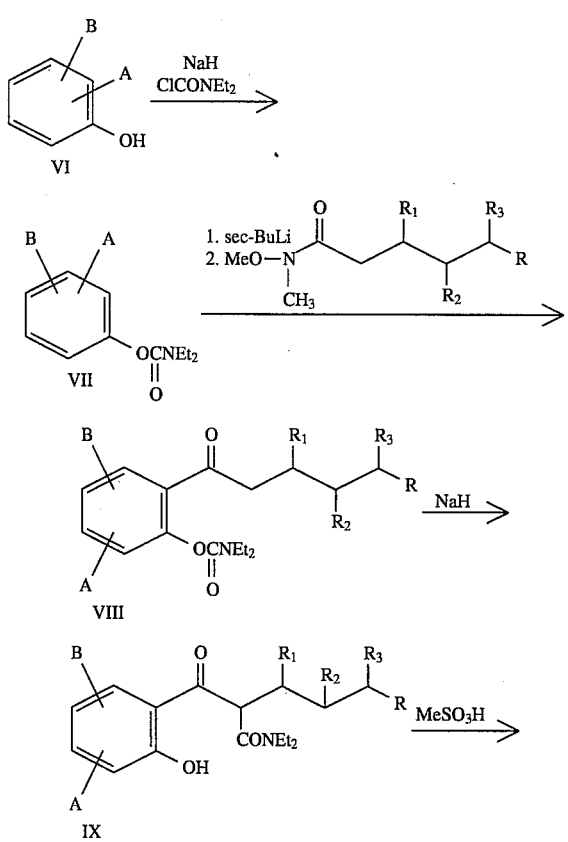

-continued
SCHEME II

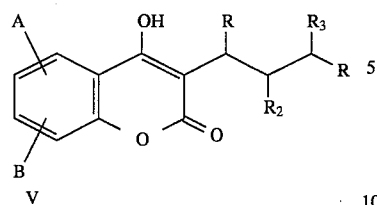

Phenol derivative VI is converted to carbamate VII, using sodium hydride and diethyl chlorocarbamate in a dry solvent, e.g. DMF (dimethylformanide), ether, or THF, at −78° C. to 0° C. The carbamate group serves as both a protecting group and an ortho-director in the next step, which involves treatment of VII with an alkyl lithium, e.g. sec-butyl lithium, in the presence of TMEDA (tetramethylethylene diamine) at −78° C. to −35° C., followed by acylation, using a suitable acylating agent such as a tertiary amide, yielding phenone VIII. Migration of the carbamoyl group may now be accomplished using excess sodium hydride, usually 2–3 equivalents. Rearrangement product IX is cyclized to the coumarin V using 1–2 equivalents of acid, e.g. methanesulfonic acid in toluene or dichloromethane, at a temperature between 25° C. and the boiling point of the reaction solvent. Several benzopyran-2-ones may also be prepared by acylation as shown in Scheme III below.

SCHEME III

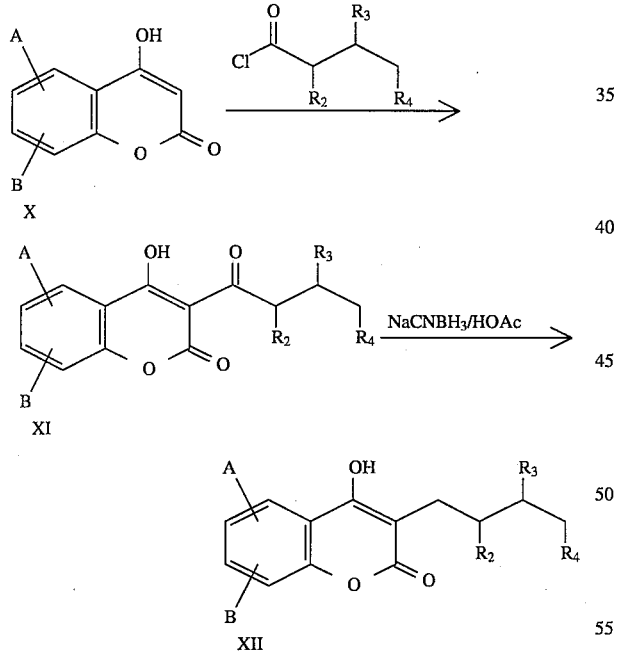

Here, a 4-hydroxycoumarin X is reacted with an excess of a suitable acid chloride in the presence of a catalytic amount of piperidine in pyridine solution, at a temperature between 25° C. and the boiling point of the reaction solvent for 3 to 24 hours, producing ketone XI. The keto group of XI is reduced to the methylene with a suitable reducing agent, such as sodium cyanoborohydride or molecular hydrogen in the presence of a suitable catalyst, furnishing coumarin XII.

Scheme IV illustrates the preparation of several thio analogues by reaction of a suitable 4-hydroxycoumarin with a suitable p-toluenethiolsulfonate, e.g. according to the procedures outlined in U.S. Pat. No. 3,810,922 (1974).

SCHEME IV

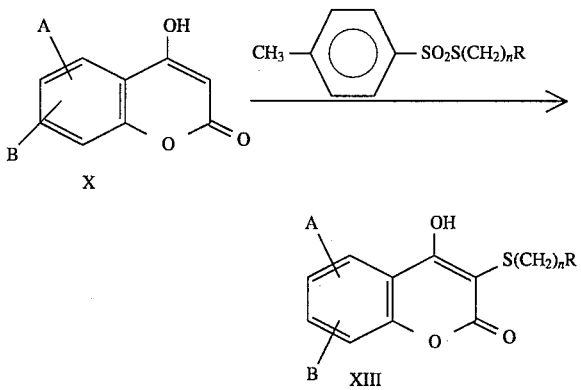

Scheme V depicts the synthesis of 4-hydroxy-2H-1-benzopyran-2-ones containing a substituted sidechain at the 3-position of the pyrone nucleus.

SCHEME V

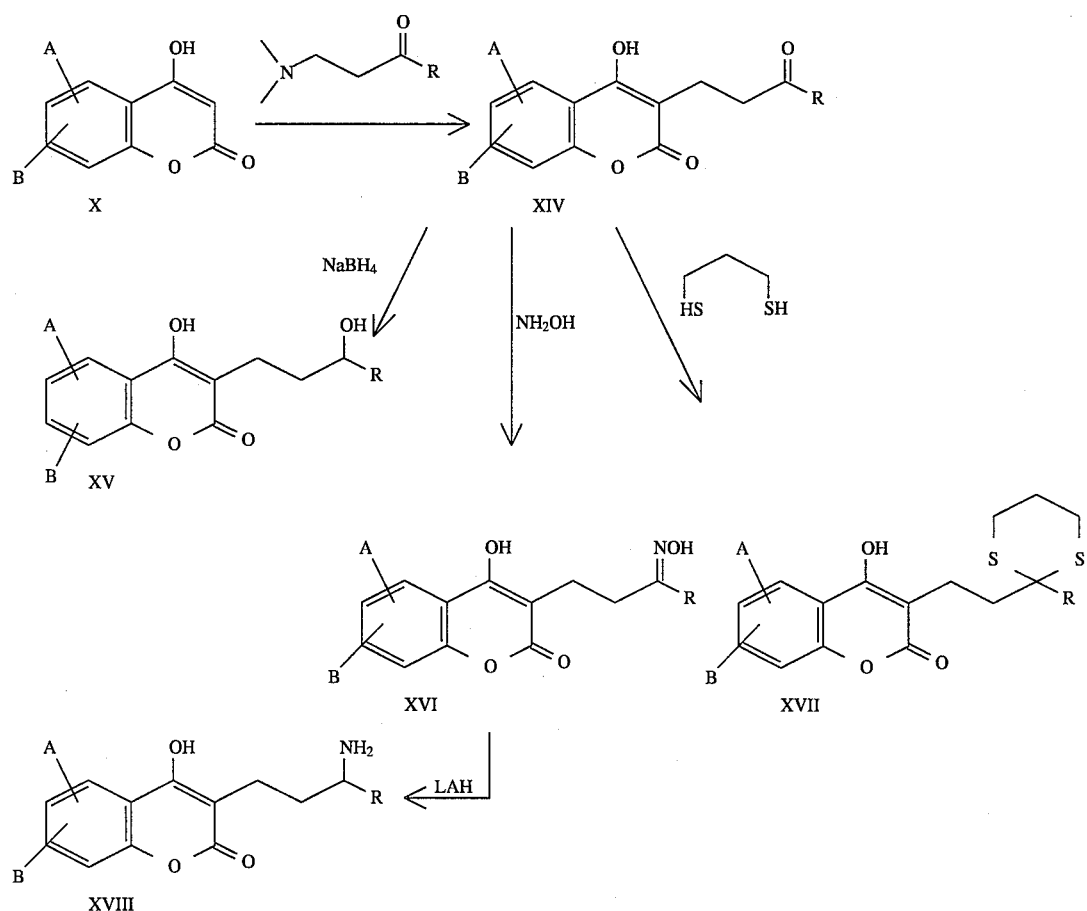

Ketone XIV is prepared from a suitable 4-hydroxycoumarin and a Mannich base, such as a β-dimethylaminoketone, as described in *Synthesis*, 894– 896 (1985), and used as a starting material for the synthesis of many derivatives. Thus, ketone XIV may be reduced to the alcohol with a borohydride, such as sodium borohydride, in a suitable solvent, e.g. methanol, THF, or ether. Alternatively, ketone may be elaborated to a thioketal XVII, by treatment with a suitable dithiol in an inert solvent, e.g. dichloromethane, in the presence of a Lewis acid catalyst, e.g. $BF_3 \cdot Et_2O$, for 3 to 24 hours. Ketone XIV may also be transformed to oxime XVI via reaction with hydroxylamine hydrochloride and a suitable base, e.g. sodium ethoxide or sodium hydroxide, in an alcoholic medium at 25° to 35° C. Oxime XVI may further be reduced using a hydride donor, e.g. lithium aluminum hydride, or catalytic hydrogenation, to the amine XVIII. These reductions usually proceed in a solvent such as THF, ether, or an alcohol, at 0° C. to room temperature. Amines XVIII may be further modified at nitrogen, using reactions well known in the art, such as alkylation, acylation and the like.

Scheme VI outlines the preparation of additional benzopyran-2-ones containing substituents at the 3-position of the pyrone nucleus.

SCHEME IV

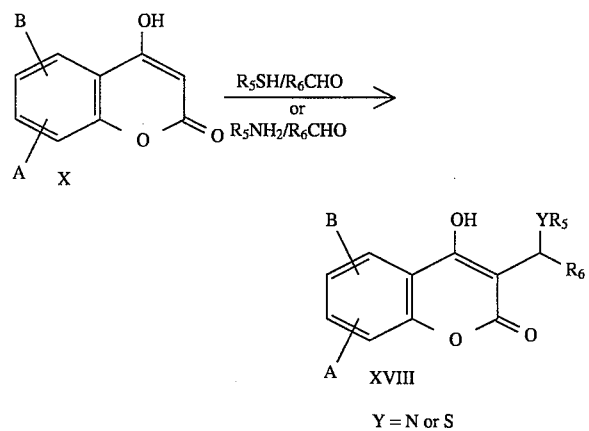

Y = N or S

Thus, 1-hydroxycoumarin X is reacted with a mixture of an appropriately substituted thiol and an aldehyde, in a suitable solvent such as ethanol or methanol containing piperidine and acetic acid, at a temperature between 25° C. and the boiling point of the reaction solvent, furnishing sulfide XVIII (Y=S). Alternatively, amine XVIII (Y=N) may be obtained as reaction product if the substituted thiol ($R_5SH$) is replaced with an appropriately substituted amine ($R_5NH_2$) and the reaction is conducted under suitable conditions.

4.2 PREPARATION OF COUMARINS

4.2.1 Preparation of Starting Materials

EXAMPLE A

2-[(2-Methoxyethoxy)methoxy]benzoic acid.

A solution of 15.2 g (100 mmol) of methyl salicylate in 60 mL of THF was cooled to 5° C. and treated portionwise with 4.0 g (100 mmol) of 60% sodium hydride. When addition was complete, the suspension was stirred another hour at 5° C. Neat MEM chloride (15 mL; 130 mmol) was added dropwise, and the reaction mixture was stirred at room temperature for two hours. Water and ethyl acetate were added; the organic layer was separated, washed with 1N sodium hydroxide and water, and dried. Concentration gave an oil which was chromatographed on silica gel, eluting with 5:1 hexane: ethyl acetate. The product so obtained was dissolved in 50 mL of methanol, treated with 50 mL of 5M sodium hydroxide, and stirred at room temperature for 18 hours. The solution was concentrated and the residue dissolved in water. The aqueous solution was washed with ether, acidified to pH 2.5 with 6N hydrochloric acid, and extracted with ether. The organic extract was washed with water, dried, and concentrated to give 16.1 g of the title compound. NMR ($CDCl_3$) δ3.37 (s, 3H), 3.58 (m, 2H), 3.90 (m, 2H), 5.50 (s, 2H), 7.15 (t, 1H), 7.29 (d, 1H), 7.53 (m, 1H), 8.12 (dd, 1H).

EXAMPLE B

2-[(2-Methoxyethoxy)methoxy]-β-oxo-benzenepropanoic acid, ethyl ester.

A solution of the product obtained in Example A (14.6 g; 64.5 mmol) in 100 mL of dry THF was treated with 12.5 g (77 mmol) of 1,1'-carbonyldiimidazole and stirred at room temperature for 6 hours. Meanwhile, a suspension of 6.14 g (64.5 mmol) of anhydrous magnesium chloride, 15.0 g (88 mmol) of potassium ethyl malonate, and 150 mL of THF was stirred at 50° C. for six hours and then cooled to room temperature. The solution of crude imidazolide was added to the solution of magnesium malonate, and the reaction mixture was stirred at room temperature for 18 hours. The solution was concentrated; the residue was partitioned between chloroform and water. The organic layer was separated, washed with 10% aqueous $KHSO_4$ and water, and dried. Concentration gave an oil which was chromatographed on silica gel, eluting with 2:1 hexane: ethyl acetate, to give 15.7 g of the title compound. NMR ($CDCl_3$) δ1.23 (t, 3H), 3.38 (s, 3H), 3.56 (m, 2H), 3.84 (m, 2H), 3.99 (s, 2H), 4.18 (q, 2H), 5.36 (s, 2H), 7.07 (t, 1H), 7.27 (d, 1H), 7.48 (m, 1H), 7.84 (dd, 1H).

EXAMPLE C

4-Methylphenyl diethylcarbamate

To a suspension of 60% sodium hydride in oil (3.8 g; 94.5 mmol) in ether (120 ml) and DMF (30 ml) was added a solution of p-cresol (9.3 g; 85.9 mmol) in ether (30 ml) dropwise. After the addition was complete the mixture was stirred 15 minutes before adding a solution of diethyl chlorocarbamate (13.9 g; 102.7 mmol) in ether (20 ml) dropwise. After the addition was complete the mixture was stirred 18 hours at room temperature before pouring onto crushed ice. The layers were separated and the organic layer was washed with aqueous 1N NaOH, water, and dried ($MgSO_4$) to provide 15.7 g of the title compound. NMR ($CDCl_3$) δ 1.2 (br m, 6H), 2.3 (s, 3H), 3.4 (br m, 4H), 6.82–7.3 (m, 4H).

EXAMPLE D

4-Chlorophenyl diethylcarbamate

The title compound was prepared from p-chlorophenol and diethyl chlorocarbamate following the same procedure used in Example C; NMR ($CDCl_3$) δ1.2 (br q, 6H), 3.4 (br t, 4H), 7.06 (m, 2H), 7.3 (m, 2H).

EXAMPLE E 4-(Phenylmethyl)phenyl diethylcarbamate

The title compound was prepared from 4-(phenylmethyl)phenol and diethyl chlorocarbamate following the same procedure used in Example C; NMR ($CDCl_3$) δ1.24 (m, 6H), 3.41 (m, 4H), 3.94 (s, 3H), 7.05–7.35 (m, 9H).

EXAMPLE F

2-[4-(2-Methoxyphenyl)-1-oxobutyl]-4-chlorophenyl diethylcarbamate

To a −78° C. solution of tetramethyl ethylenediamine 0.55 g (4.8 mmol) in dry tetrahydrofuran (5 ml) was added 4.6 mmol of sec-butyl lithium dropwise. The resulting solution was stirred 10 min. at −78° C. and then a solution of 4-chlorophenyl diethylcarbamate (1.0 g; 4.4 mmol) in 10 ml of tetrahydrofuran was added dropwise. The resulting solution was stirred 3 hours at −78° C. before adding a solution of N-methoxy-N-methyl-5-phenoxy pentanamide, (1.4 g; 5.7 mmol), in tetrahydrofuran (3 ml). The mixture was allowed to stir for 2 hours at −78° C. followed by addition of acetic acid [0.42 g; 7 mmol] in ether (2 ml). The mixture was allowed to warm to room temperature and then poured onto water. The product was extracted with ether (2×). The organic layers were combined, washed with saturated aqueous NaCl, and dried ($MgSO_4$). The crude product was chromatographed on silica gel (E. Merck, 230–400 Mesh), eluting with ethyl acetate/hexane to give 0.45 g of the title compound. NMR ($CDCl_3$) δ1.18 (t, 3 H), 1.26 (t, 3H), 1.85 (m, 4H), 2.94 (t, 2H), 3.34 (q, 2H), 3.45 (q, 2H), 3.97 (t, 2H), 6.67–7.44 (m, 7H), 7.63 (d, 1H).

EXAMPLE G 2-(1-Oxo-5-phenoxypentyl)-4-(phenylmethyl)phenyl diethylcarbamate The title compound was prepared from 4-(phenylmethyl)phenyl diethylcarbamate and N-methoxy-N-methyl-5-phenoxypentanamide following the same procedure used in Example F. NMR ($CDCl_3$) δ1.18 (t, 3 H), 1.26 (t, 3H), 1.83 (m, 4H), 2.92 (t, 2H), 3.35 (q, 2H), 3.45 (q, 2H) 3.99 (m, 4H), 6.86–7.31 (m, 12H), 7.49 (d, 1H).

EXAMPLE H 2-(1-Oxo-5-phenoxypentyl)-4-methylphenyl diethylcarbamate

The title compound was prepared from 4-methylphenyl diethylcarbamate and N-methoxy-N-methyl- 5-phenoxypentanamide following the same procedure used in Example F.

EXAMPLE I

N,N-Diethyl-2-hydroxy-5-chloro-β-oxo-α-(3-phenoxypropyl)benzenepropanamide

To a solution of 2-[4-(2-methoxyphenyl)-1-oxobutyl]-4-chlorophenyldiethyl carbamate (0.5 g; 1.3 mmol) in tetrahydrofuran (5 ml) was added sodium hydride (60% suspension in oil, 2.7 mmol). The resulting mixture was stirred 5 hours at room temperature. The mixture was poured into water, and aqueous 2M HCl was added until the mixture was acidic. The product was extracted with ether (2×), and the combined organic layers were washed with saturated aqueous NaCl, and dried (MgSO$_4$). The product was purified by flash chromatography on silica gel (E. Merck, 230–400 mesh), eluting with ethyl acetate/hexane to give 0.33 g of the title compound.

EXAMPLE J

N,N-Diethyl-2-hydroxy-β-oxo-α-(3-phenoxypropyl)-5-(phenylmethyl)benzenepropanamide The title compound was prepared from 2-(1-oxo-5-phenoxypentyl)-4-(phenylmethyl)phenyl diethylcarbamate following the same procedure used in Example I. NMR (CDCl$_3$) δ1.08 (m, 6H), 1.88 (m, 2H), 2.19 (m, 2H), 3.19–3.45 (m, 6H), 3.86 (s, 2H), 3.95–4.13 (m, 2H), 4.45 (t, 1H), 6.83 (m, 2H), 6.93 (m, 2H), 7.09–7.34 (m, 8H), 7.54 (s, 1H), 12.03 (br s, 1H).

EXAMPLE K

N,N-Diethyl-2-hydroxy-5-methyl-β-oxo-α(3-phenoxypropyl)bensenepropanamide

The title compound was prepared from 2-(1-oxo-5-phenoxypentyl)-4-methylphenyl diethylcarbamate following the same procedure used in Example I.

4.2.2. Preparation of Specific Coumarin Derivatives

EXAMPLE 1

3-[3-(4-Fluorophenoxy)propyl]-4-hydroxy-2H-1-bensopyran-2-one

To a solution of sodium ethoxide in ethanol (0.51 g of sodium in 5 mL of anhydrous ethanol) was added a solution of 0.62 g (2.1 mmol) of the ketoester of Example B. The mixture was stirred at room temperature for one hour and then treated with 0.54 g (2.3 mmol) of 3-(4-fluorophenoxy)propyl bromide and with 0.34 g (2.3 mmol) of sodium iodide. The suspension was refluxed for 10 hours, cooled to room temperature, and concentrated. The residue was partitioned between ether and water; the organic layer was dried over magnesium sulfate and concentrated. The crude product was chromatographed over silica gel (E. Merck, 230–400 Mesh), eluting with 2:1 hexane: ethyl acetate, to give 0.60 g of oil. This material was dissolved in 30 mL of dichloromethane, treated with 1 mL of trifluoroacetic acid, and stirred for 12 hours. Concentration gave a residue which was triturated with 1:1 hexane: ether. The solids were filtered, washed with hexane, and dried to give 0.28 g of the title compound, m.p. 155°–156° C. NMR (DMSO-d$_6$) δ1.89 (m, 2H), 2.67 (t, 2H), 3.97 (t, 2H), 6.92 (m, 2H), 7.09 (t, 2H), 7.35 (m, 2H), 7.59 (t, 1H), 7.94 (d, 1H).

EXAMPLE 2

4-Hydroxy-3-[3-(4-nitrophenoxy)propyl]-2H-1-benzopyran-2-one

The title compound was prepared from the ketoester of Example B and 3-(4-nitrophenoxy)propyl bromide following the same procedure used in Example 1; m.p. 225°–226° C. NMR (DMSO-d$_6$) δ1.96 (m, 2H), 2.70 (t, 2H), 4.16 (t, 2H), 7.11 (d, 2H), 7.35 (m, 2H), 7.60 (t, 1H), 7.93 (dd, 1H), 8.19 (d, 2H), 11.40 (bs, 1H).

EXAMPLE 3

4-Hydroxy-3-(2-phenoxyethyl)-2H-1-benzopyran-2-one

The title compound was prepared from the ketoester of Example B and 2-phenoxyethyl bromide following the same procedure used in Example 1; m.p. 157°–159° C. NMR (DMSO-d$_6$) δ3.01 (t, 2H), 4.05 (t, 2 H), 6.92 (m, 3H), 7.27 (m, 2H), 7.36 (m, 2H), 7.61 (m, 1H), 7.95 (d, 1H), 11.66 (bs, 1H).

EXAMPLE 4

4-Hydroxy-3-[3-(4-methoxyphenoxy)propyl]-2H-1-bensopyran-2-one

The title compound was prepared from the ketoester of Example B and 3-(4-methoxyphenoxy)propyl bromide following the same procedure used in Example 1; m.p. 111°–112° C. NMR (DMSO-d$_6$) δ1.88 (m, 2H), 2.67 (m, 2H), 3.69 (s, 3H), 3.93 (t, 2H), 6.84 (s, 4H), 7.35 (m, 2H), 7.61 (t, 1H), 7.93 (dd, 1H).

EXAMPLE 5

4-Hydroxy-3-[3-(3-methoxyphenoxy)propyl]-2H-1-benzopyran-2-one

The title compound was prepared from the ketoester of Example B and 3-(3-methoxyphenoxy)propyl bromide following the same procedure used in Example 1; m.p. 115°–117° C.

EXAMPLE 6

4-Hydroxy-3-[3-(2-methoxyphenoxy)propyl]-2H-1-bensopyran-2-one

The title compound was prepared from the ketoester of Example B and 3-(2-methoxyphenoxy)propyl bromide following the same procedure used in Example 1; m.p. 119°–120° C. NMR (DMSO-d$_6$) δ1.91 (m, 2H), 2.66 (t, 2H), 3.68 (s, 3H), 3.98 (t, 2H), 6.83–6.95 (m, 4H), 7.34 (m, 2H), 7.59 (t, 1H), 7.93 (dd, 1 H).

EXAMPLE 7

3-[3-(3-Chlorophenoxy)propyl]-4-hydroxy-2H-1-benzopyran-2-one

The title compound was prepared from the ketoester of Example B and 3-(3-chlorophenoxy)propyl bromide following the procedure used in Example 1; m.p. 169°–171° C. NMR (DMSO-d$_6$) δ1.91 (m, 2H), 2.67 (t, 2H), 4.02 (t, 2H), 6.87 (m, 1H), 6.96 (m, 2H), 7.28 (m, 1H), 7.36 (d, 2H), 7.60 (t, 1H), 7.93 (dd, 1H), 11.37 (bs, 1H).

EXAMPLE 8

Ethyl 3-[3-(4-hydroxy-2-oxo-2H-1-benzopyran-3-yl)propoxy]benzoate

The title compound was prepared from the ketoester of Example B and ethyl 3-(3-bromopropoxy)benzoate following the procedure used in Example 1; m.p. 125°–126° C. NMR (DMSO-d$_6$) δ1.31 (t, 3 H), 1.93 (m, 2H), 2.69 (t, 2H), 4.06 (t, 2H), 4.29 (q, 2H), 7.18 (m, 1H), 7.32–7.44 (m, 4H), 7.53 (m, 1H), 7.60 (m, 1H), 7.93 (dd, 1H), 11.36 (bs, 1H).

EXAMPLE 9

3-[3-(4-Hydroxy-2-oxo-2H-1-benzopyran-3-yl)propoxy]benzoic acid

A suspension of 0.37 g (1.0 mmol) of the compound prepared in Example 8 in 10 mL of ethanol was treated with 1 mL of 20% sodium hydroxide and stirred at room temperature for 18 hours. The solution was concentrated, and the residue was dissolved in water and washed with ether. The aqueous phase was acidified to pH 4 with 6N hydrochloric acid and filtered. The solids were washed with water and dried to give the title compound, m.p. 242°–244° C. NMR (DMSO-$d_6$) $\delta$1.93 (m, 2H), 2.69 (t, 2H), 4.05 (t, 2H), 7.16 (m, 1H), 7.32–7.42 (m, 4H), 7.54 (m, 1H), 7.58 (m, 1H), 7.93 (dd, 1H), 11.50 (bs, 1H), 12.97 (bs, 1H).

EXAMPLE 10

4-Hydroxy-3-[3-(3-hydroxymethylphenoxy)propyl]-2H-1-benzopyran-2-one

A solution of 0.48 g (1.3 mmol) of the compound prepared in Example 8 in 40 mL of dry THF was cooled in an ice bath and treated with 1.0 g (26 mmol) of lithium aluminum hydride. The suspension was stirred at 5° C. for thirty minutes and at room temperature for 3 hours. To the mixture were added 0.8 mL of water, 1.0 mL of 20% sodium hydroxide, and 3.6 mL of water, in that order. The mixture was stirred for thirty minutes and filtered, and the filtrate was concentrated. The residue was chromatographed on silica gel (E. Merck 240–400 ASTM), eluting with 9:1 chloroform: methanol, to give 0.19 g of the title compound, m.p. 119°–121° C. NMR (DMSO-$d_6$) $\delta$1.91 (m, 2 H), 2.68 (t, 2H), 3.99 (t, 2H), 4.45 (s, 2H), 5.15 (bs, 1H), 6.76 (d, 1H), 6.86 (m, 2H), 7.20 (t, 1 H), 7.35 (m, 2H), 7.59 (m,1H), 7.94 (dd, 1H).

EXAMPLE 11

4-Hydroxy-3-[3-(phenylthio)propyl]-2H-1-benzopyran-2-one

The title compound was prepared from the ketoester of Example B and 3-(phenylthio)propyl bromide following the same procedure used in Example 1; m.p.156°–157° C. NMR (DMSO-$d_6$) $\delta$1.75 (m, 2H), 2.64 (t, 2H), 2.98 (t, 2H), 7.17 (m, 1H), 7.27–7.36 (m, 6H), 7.58 (t, 1H), 7.92 (dd, 1H).

EXAMPLE 12

4-Hydroxy-3-[3-(3-nitrophenoxy)propyl]-2H-1-benzopyran-2-one

The title compound was prepared from the ketoester of Example B and 3-(3-nitrophenoxy)propyl bromide following the same procedure used in Example 1; m.p. 175°–177° C. NMR (DMSO-$d_6$) $\delta$1.95 (m, 2H), 2.70 (t, 2H), 4.13 (t, 2H), 7.37 (m, 3H), 7.55 (m, 2H), 7.66 (t, 1H), 7.79 (m, 1H), 7.93 (dd, 1H), 11.37 (bs, 1H).

EXAMPLE 13

4-Hydroxy-3-[4-(2-methoxyphenyl)butyl]-2H-1-benzopyran-2-one

A solution of 2.91 g (15.0 mmol) of 4-(2-methoxyphenyl)butanoic acid, 1.7 mL (19 mmol) of oxalyl chloride, and 40 mL of dichloromethane was treated with 3 drops of DMF. The reaction mixture was stirred at room temperature for 2 hours and concentrated. This crude acid chloride was added dropwise to a solution of 2.43 g (15.0 mmol) of 4-hydroxycoumarin, 10 drops of piperidine, and 40 mL of pyridine. The resulting mixture was refluxed for 18 hours, then cooled to room temperature and poured into ice water. The suspension was acidified to pH 2 with 6N hydrochloric acid. The solids obtained were filtered, washed with water, and dried. Recrystallization from ethanol gave 2.7 g of the acyl compound; NMR (CDCl$_3$) $\delta$2.02 (m, 2H), 2.74 (t, 2H), 3.25 (t, 2H), 3.81 (s, 3H), 6.82–6.90 (m, 2H), 7.16 (m, 2H), 7.26–7.52 (m, 2H), 7.69 (t, 1H), 8.06 (d, 1H).

A solution of 1.02 g (3.01 mmol) of the product obtained above in 10 mL of acetic acid was heated to 100° C. and treated portionwise with 0.40 g (6.4 mmol) of sodium cyanoborohydride. The mixture was stirred at room temperature for 1 hour. Water (20 mL) was added, and the solids were filtered and washed with water. Recrystallization from ethanol: water gave 0.75 g of the title compound, m.p. 123°–124° C.; NMR (DMSO-$d_6$) $\delta$1.63 (m, 4H), 2.64 (t, 4H), 3.80 (s, 3 H), 6.85 (t, 2H), 7.13 (d, 2H), 7.27 (d, 2H), 7.48 (t, 1H), 7.92 (d, 1H).

EXAMPLE 14

4-Hydroxy-3-[4-(2-hydroxyphenyl)butyl]-2H-1-benzopyran-2-one

A solution of 0.58 g (1.8 mmol) of the product obtained in Example 13 in 20 mL of dichloromethane was cooled to −78° C. and treated with 1.0 mL (11 mmol) of neat boron tribromide. The reaction mixture was allowed to warm to 0° C. over two hours. Ice water was added, and the suspension was extracted with ethyl acetate. The organic extract was washed with water, dried over magnesium sulfate, and concentrated. The residue was chromatographed over silica gel, eluting with 4:1 hexane: ethyl acetate, to give 0.42 g of the title compound, m.p. 131°–133° C.; NMR (DMSO-$d_6$) $\delta$1.60 (m, 2H), 1.70 (m, 2H), 2.65 (m, 4H), 6.84–6.72 (m, 2H), 6.99 (t, 1H), 7.06 (d, 1H), 7.24 (d, 2H), 7.48 (t, 1H), 7.91 (d, 1H).

EXAMPLE 15

3-(4-Cyclohexylbutyl)-4-hydroxy-2H-1-benzopyran-2-one

The title compound was prepared from 4-cyclohexylbutyryl chloride and 4-hydroxycoumarin following the same procedure used in Example 13, m.p. 160°–161° C.; NMR (CDCl$_3$) $\delta$0.82 (m, 2H), 1.15 (m, 5H), 1.38 (m, 2H), 1.51–1.66 (m, 8H), 2.62 (t, 2H), 7.21 (bs, 1H), 7.26–7.34 (m, 2H), 7.53 (m, 1H), 7.87 (dd, 1H).

EXAMPLE 16

4-Hydroxy-3-(3-oxo-3-phenylpropyl)-2H-1-benzopyran-2-one

A solution of 0.81 g (5.0 mmol) of 4-hydroxycoumarin, 1.07 g ( 5.0 mmol) of 2-dimethylaminopropiophenone, and 20 mL of acetonitrile was treated with 0.2 mL (5.0 mmol) of triethylamine and then refluxed for 4 hours. The mixture was cooled to room temperature and poured into 5% sodium hydroxide. The aqueous solution was extracted with ether and acidified to pH 3 with 6N hydrochloric acid. The mixture was extracted with chloroform, and the extract was washed with water, dried, and concentrated to give the title compound, m.p. 149°– 151° C. NMR (CDCl$_3$) δ2.99 (m, 2H), 3.52 (m, 2H), 7.26 (m, 2H), 7.48 (m, 3H), 7.60 (m, 1H), 7.94 (dd, 1H), 8.02 (d, 2H), 10.65 (bs, 1H).

EXAMPLE 17

4-Hydroxy-3-(3-hydroxy-3-phenylpropyl)-2H-1-benzopyran-2-one

A rapidly stirred suspension of the product obtained in Example 16 (0.21 g, 0.71 mmol) in 10 mL of methanol was treated portionwise with 0.08 g (2.1 mmol) of sodium borohydride. The reaction mixture was stirred at room temperature for 36 hours. Glacial 30 acetic acid (3 mL) was added, and the mixture was concentrated. The residue was partitioned between ethyl acetate and water, and the organic layer was dried and concentrated. The product was chromatographed on silica gel, eluting with 4:1 chloroform: ethyl acetate, to give the title compound, m.p. 138°–140° C. NMR (CDCl$_3$) δ1.25 (m, 2 H), 2.88 (m, 2H), 4.66 (dd, 1H), 7.32 (m, 7H), 7.52 (t, 1H), 7.90 (d, 1H).

EXAMPLE 18

4-Hydroxy-3-[(3-hydroxyimino)-3-phenylpropyl)]-2H-1-benzopyran-2-one

Hydroxylamine hydrochloride (0.06 g; 0.9 mmol) was added portionwise to a solution of sodium methoxide in methanol (0.02 g Na in 10 mL of methanol); when addition was complete, the product isolated in Example 16 (0.21 g; 0.71 mmol) was added portionwise to the reaction mixture and stirred at room temperature for 18 hours. The solution was concentrated, and the residue was partitioned between chloroform and water. The organic layer was dried and concentrated. The product was recrystallized from ethyl acetate: hexane to give the title compound. NMR (DMSO-d$_6$) δ2.74 (m, 2H), 2.94 (m, 2H), 7.35 (m, 5 H), 7.58 (t, 1H), 7.74 (m, 2H), 7.96 (d, 1H).

EXAMPLE 19

4-Hydroxy-3-[(phenylmethyl)thio]2H-1-benzopyran-2-one

The title compound was prepared as described in U.S. Pat. No. 3,810,922 (1974), m.p. 157°–158° C.

EXAMPLE 20

4-Hydroxy-3-[(3-phenylpropyl)thio]-2H-1-benzopyran-2-one

A solution of 0.65 g (4.0 mmol) of 4-hydroxycoumarin in ethanol (30 mL) was treated with a solution of 0.16 g (4.0 mmol) of NaOH in water (10 mL) and then with 1.22 g (4.0 mmol) of 3-phenylpropyl p-toluenethiolsulfonate. The mixture was refluxed for 18 hours, cooled to room temperature, and concentrated. The residue was partitioned between chloroform and water. The organic layer was dried and concentrated. The product was chromatographed on silica gel, eluting with 10:1 hexane: ethyl acetate, to give 0.65 g of the title compound, m.p. 74°–75° C. NMR (CDCl$_3$) δ1.90 (m, 2H), 2.73 (t, 2H), 2.84 (t, 2 H), 7.11–7.37 (m, 7H), 7.58 (t, 1H), 7.90 (d, 1H).

EXAMPLE 21

4-Hydroxy-3-(2-phenoxyethylthio)-2H-1-benzopyran-2-one

The title compound was prepared as described in Example 20 from 4-hydroxycoumarin and 2-phenoxyethyl p-toluenethiolsulfonate; m.p. 120°–121° C. NMR (CDCl$_3$) δ3.21 (t, 2H), 4.11 (t, 2H), 6.86 (d, 2H), 6.97 (t, 1H), 7.25–7.37 (m, 4H), 7.62 (d, 1H), 7.88 (d, 1H), 8.39 (bs, 1H).

EXAMPLE 22

4-Hydroxy-7-methoxy-3-[4-(2-methoxyphenyl)butyl]-2H-1 -benzopyran-2-one

The title compound was prepared from 4-hydroxy-7-methoxy-2H-1-benzopyran-2-one and 4-(2-methoxyphenyl)butanoic acid using the procedure described in Example 13. The product was obtained 41% yield, m.p. 153°– 153.5° C. NMR (DMSO-d$_6$) δ1.42–1.57 (m, 4H), 2.42– 2.57 (m, 4H), 3.75 (s, 3H), 3.84 (s, 3H), 6.83 (t, 1H), 6.93 (m, 3H), 7.09–7.17 (m, 2H), 7.81 (m, 1 H).

EXAMPLE 23

4-Hydroxy-3-[4-(2-methoxyphenyl)butyl]-8-methyl-2H-1-benzopyran-2-one

The title compound was prepared from 4-hydroxy-8 -methyl-2H-1-benzopyran-2-one and 4-(2-methoxyphenyl)butanoic acid using the procedure described in Example 13. The product was obtained 59% yield, m.p. 163°–165° C. NMR (DMSO-d$_6$) δ1.44–1.57 (m, 4H), 2.35 (s, 3H), 2.50–2.57 (m, 4H), 3.75 (s, 3H), 6.83 (t, 1H), 6.91 (d, 1H), 7.09–7.25 (m, 3H), 7.45 (d, 1 H), 7.74 (d, 1H).

EXAMPLE 24

4-Hydroxy-3-[4-(2-methoxyphenyl)butyl]-8-methyl-7-phenylmethoxy)-2H-1-benzopyran-2-one The title compound was prepared from 4-hydroxy-8 -methyl-7-(phenylmethoxy)-2H-1-benzopyran-2-one, and 4 -(2-methoxyphenyl)butanoic acid using the procedure described in Example 13. A 53% yield of the title compound was obtained: m.p. 161°–162° C. NMR (DMSO-d$_6$) δ1.43–1.55 (m, 4H), 2.49–2.57 (m, 6H), 3.75 (s, 3 H), 5.25 (s, 2H), 6.83 (t, 1H), 6.91 (d, 1H), 7.11– 7.32 (m, 3H), 7.32–7.49 (m, 5H), 7.73 (d, 2H), 11.02 (br s, 1H).

EXAMPLE 25

4-Hydroxy-3-[4-(2-methoxyphenyl)butyl]-6-phenyl-2H-1-benzopyran-2-one

The title compound was prepared from 4-hydroxy-6 -phenyl-2H-1-benzopyran-2-one and 4-(2-methoxyphenyl)butanoic acid using the procedure described in Example 13. A 43% yield of the title compound was obtained: m.p. 181°–182° C. NMR (DMSO-d$_6$) δ1.48–1.59 (m, 4H), 2.50–2.59 (m, 4H), 3.76 (s, 3H), 6.34 (t, 1H), 6.92 (d, 1H), 7.11–7.17 (m, 2H), 7.38–7.52 (m, 4H), 7.72 (d, 2H), 7.89 (dd, 1H), 8.19 (d, 1H).

EXAMPLE 26

4-Hydroxy-3-[4-(2-methoxyphenyl)butyl]-8-phenyl-2H-1-benzopyran-2-one

The title compound was prepared from 4-hydroxy-8-phenyl-2H-1-benzopyran-2-one, and 4-(2-methoxyphenyl)butanoic acid using the procedure described in Example 13. A 64% yield of the title compound was obtained: m.p. 142°–143° C. NMR (DMSO-$d_6$) $\delta$1.43–1.59 (m, 4H), 2.51–2.57 (m, 4H), 3.75 (s, 3H), 6.83 (t, 1H), 6.91 (d, 1H), 7.09–7.17 (m, 2H), 7.39–7.61 (m, 7H), 7.92 (dd, 1H) 11.2 (br s, 1H).

EXAMPLE 27

6-Bromo-4-hydroxy-3-[4-(2-methoxyphenyl)butyl]-2H-1-benzopyran-2-one

The title compound was prepared from 4-hydroxy-6-bromo-2H-1-benzopyran-2-one, and 4-(2-methoxyphenyl)butanoic acid using the procedure described in Example 13. A 55% yield of the title compound was obtained, m.p. 147.5°–148.5° C.

EXAMPLE 28

4-Hydroxy-3-[4-(2-methoxyphenyl)butyl]-6-methyl-2H-1-benzopyran-2-one

The title compound was prepared from 4-hydroxy-6-methyl-2H-1-benzopyran-2-one and 4-(2-methoxyphenyl)butanoic acid using the procedure described in Example 13. A 46% yield of the title compound was obtained, m.p. 154°–155° C.

EXAMPLE 29

6-Chloro-4-hydroxy-3-(3-phenoxypropyl)-2H-1-benzopyran-2-one

To a solution of N,N-diethyl-2-hydroxy-5-chloro-$\beta$-oxo-$\alpha$-(3-phenoxypropyl)benzenepropanamide (0.25 g; 6.6 mmol) (prepared in Example I) in toluene (5 ml) was added methanesulfonic acid (0.07 g; 0.7 mmol). The resulting mixture was heated to reflux and stirred for 20 minutes. The mixture was cooled and the solvent removed under reduced pressure. The residue was dissolved in a 1:1 mixture of EtOAc/Et$_2$O (10 ml), washed with saturated aqueous NaCl, and dried (MgSO$_4$). The solvent was removed in vacuo to provide an oil which crystallized from Et$_2$O to provide 0.16 g (83% yield) of the title compound, m.p. 162°–163° C. NMR (DMSO-$d_6$) $\delta$1.90 (m, 2H), 2.68 (t, 2H), 3.99 (t, 2H), 6.91 (m, 3H), 7.26 (m, 2H), 7.41 (d, 1H), 7.63 (dd, 1H), 7.95 (d, 1H).

EXAMPLE 30

4-Hydroxy-3-(3-phenoxypropyl)-6-(phenylmethyl)-2H-1-benzopyran-2-one

The title compound was prepared from N,N-diethyl-2-hydroxy-$\beta$-oxo-$\alpha$-(3-phenoxypropyl)-5-(phenylmethyl)benzenepropanamide (prepared in Example J) following the same procedure used in Example 29. m.p. 149°–150° C. NMR (DMSO-$d_6$) $\delta$1.89 (m, 2H), 2.67 (t, 2H), 3.97–4.06 (m, 4H), 6.90 (m, 2H), 7.17–7.32 (m, 9H), 7.44 (m, 1H), 7.81 (m, 1 H), 11.29 (br s, 1H).

EXAMPLE 31

4-Hydroxy-6-methyl-3-(3-phenoxypropyl)-2H-1-benzopyran-2-one

The title compound was prepared from N,N-diethyl-2-hydroxy-$\beta$-oxo-$\alpha$-(3-phenoxypropyl)-5-methylbenzenepropanamide (prepared in Example K) following the same procedure used in Example 29.

EXAMPLE 32

4-Hydroxy-3-[2-(phenylmethoxy)ethyl]-2H-1-benzopyran-2-one

The title compound was prepared from the ketoester synthesized in Example B and 2-(phenylmethoxy)ethyl iodide following the same procedure used in Example 1. The title compound was isolated as an oil: NMR (DMSO-$d_6$) $\delta$2.86 (t, 2H), 3.55 (t, 2H), 4.49 (s, 2H), 7.23–7.38 (m, 7H), 7.60 (m, 1H), 7.92 (dd, 1H).

EXAMPLE 33

3-[3-(3-Aminophenoxy)propyl]-4-hydroxy-2H-1-benzopyran-2-one

The compound isolated in Example 12 (0.34 g; 1.0 mmol) was suspended in ethanol (10 mL) and water (10 mL) and was treated with 0.17 g (3.0 mmol) of iron filings. The suspension was heated to reflux, and 0.2 mL of 1N HCl was added slowly. The reaction mixture was refluxed for three hours and then filtered while hot. The filtrate was concentrated. The residue was chromatographed on silica gel, eluting with 9:1 chloroform: methanol, to give the title compound; m.p. 161°–162° C. NMR (DMSO-$d_6$) $\delta$1.87 (m, 2H), 2.65 (t, 2H), 3.88 (t, 2H), 6.05 (dd, 1H), 6.12 (m, 2 H), 6.87 (m, 1H), 7.35 (m, 2H), 7.59 (t, 1H), 7.94 (dd, 1H).

EXAMPLE 34

3-[3-(Cyclohexyloxy)propyl]-4-hydroxy-2H-1-benzopyran-2-one

The title compound was prepared from the ketoester synthesized in Example B and 3-cyclohexyloxypropyl iodide following the same procedure used in Example 1; m.p. 54°–56° C. NMR (DMSO-$d_6$) $\delta$1.18 (m, 5H), 1.45 (m, 1H), 1.66 (m, 4H), 1.80 (m, 2H), 2.54 (t, 2H), 3.27 (m, 1H), 3.41 (t, 2H), 7.36 (m, 2H), 7.58 (m, 1H), 7.92 (dd, 1H).

EXAMPLE 35

3-[3-[(4-Fluorophenyl)phenylamino]-4-hydroxy-2H-1-benzopyran-2-one

The title compound was prepared from the ketoester synthesized in Example B and 4-fluoro-N-3-iodopropyl-N-phenylbenzenamine following the same procedure used in Example 1; m.p. 143°–145° C. NMR (DMSO) $\delta$1.90 (m, 2H), 2.66 (t, 2H), 3.57 (t, 2H), 7.00–7.35 (m, 10H), 7.52 (m,1H), 7.79 (dd, 1H).

EXAMPLE 36

4-Hydroxy-3-[3-(phenylmethoxy)propyl]-2H-1-benzopyran-2-one

The title compound was prepared from the ketoester synthesized in Example B and 3-(phenylmethoxy)propyl iodide following the same procedure used in Example 1; m.p. 86°–87° C. NMR (DMSO-$d_6$) δ1.74 (m, 2H), 2.58 (t, 2H), 3.47 (t, 2 H), 4.45 (s, 2H), 7.24–7.36 (m, 7H), 7.58 (m, 1H), 7.92 (dd, 1H).

EXAMPLE 37

3-[3-(3-Cyanophenoxy)propyl]-4-hydroxy-2H-1-benzopyran-2-one

The title compound was prepared from the ketoester synthesized in Example B and 3-(3-cyanophenoxy)propyl bromide following the same procedure used in Example 1; m.p. 174°–176° C. NMR (DMSO-$d_6$) δ1.92 (m, 2H), 2.68 (t, 2H), 4.07 (t, 2 H), 7.25 (m, 1H), 7.37 (m, 4H), 7.45 (t, 1H), 7.60 (m, 1H), 7.94 (dd, 1H).

EXAMPLE 38

3-[3-(4-Chlorophenoxy)propyl]-4-hydroxy-2H-1-benzopyran-2-one

The title compound was prepared from the ketoester synthesized in Example B and 3-(4-chlorophenoxy)propyl bromide following the same procedure used in Example 1; m.p. 168°–169° C. NMR (DMSO-$d_6$) δ1.92 (m, 2H), 2.68 (t, 2H), 4.00 (t, 2H), 6.93 (d, 2H), 7.29–7.37 (m, 4H), 7.60 (m, i H), 7.94 (dd, 1H).

EXAMPLE 39

3-[3-(2-Chlorophenoxy)propyl]-4-hydroxy-2H-1-benzopyran-2-one

The title compound was prepared from the ketoester synthesized in Example B and 3-(2-chlorophenoxy)propyl bromide following the same procedure used in Example 1; m.p. 165°–167° C. NMR (DMSO-$d_6$) δ1.96 (m, 2H), 2.71 (t, 2H), 4.10 (t, 2 H), 6.93 (t, 1H), 7.12 (d, 1H), 7.25–7.42 (m, 4H), 7.60 (t, 1H), 7.95 (dd, 1H).

EXAMPLE 40

4-Hydroxy-3-[3-[(phenylmethyl)phenylamino]propyl]-2H-1-benzopyran-2-one

The title compound was prepared from the ketoester synthesized in Example B and N-(3-bromopropyl)-N-phenylmethylbenzenamine following the same procedure used in Example 1; m.p. 63°–65° C. NMR (DMSO-$d_6$) δ1.78 (m, 2H), 2.56 (t, 2H), 3.44 (t, 2 H), 4.54 (s, 2H), 6.55 (t, 1H), 6.64 (d, 2H), 7.08 (t, 2H), 7.20 (m, 3H), 7.30 (m, 2H), 7.35 (d, 2H), 7.58 (m, 1H), 7.91 (dd, 1H).

EXAMPLE 41

3-[3-(4-Hydroxy-2-oxo-2H-1-benzopyran-3-yl)propoxy]benzamide

A solution of 0.27 g (0.84 mmol) of the compound isolated in Example 37 was dissolved in 25 mL of dry t-butanol and treated with 0.24 g (4.2 mmol) of potassium hydroxide. The mixture was refluxed for 2 hours, cooled to room temperature, and concentrated. The residue was dissolved in water, washed with ether, and acidified to pH 2 with 6M HCl. The solids which precipitated were filtered, washed with ethanol-ether, and dried in vacuo to give the title compound, m.p. 197°–198° C. NMR (DMSO-$d_6$) δ1.93 (m, 2H), 2.70 (t, 2 H), 4.05 (t, 2H), 7.06 (m, 1H), 7.28–7.47 (m, 4H), 7.60 (t, 1H), 7.96 (m, 2H).

EXAMPLE 42

3-[(Cyclohexylthio)phenylmethyl]-4-hydroxy-2H-1-benzopyran-2-one

A solution of 2.0 g (6.2 mmol) of 4-hydroxy-2H-1-benzopyran-2-one in 30 mL of ethanol was treated with 0.72 g (6.8 mmol) of benzaldehyde, 1.9 g (16 mmol) of cyclohexylmercaptan, 5.0. mL of piperidine, and 5.0 mL of acetic acid. The reaction mixture was stirred at 80° C. for 24 hours. The ethanol was evaporated, and the residue was acidified with 1N HCl. The product was chromatographed on silica gel to give the title compound, m.p. 122°–124° C. NMR (DMSO-$d_6$) δ1.25 (m, 5 H), 1.56 (m, 1H), 1.67 (m, 2H), 1.94 (m, 2H), 2.72 (m, 1H), 5.58 (s, 1H), 7.17 (m, 1H), 7.28 (t, 2H), 7.39 (m, 2H), 7.53 (d, 2H), 7.64 (t, 1H), 8.03 (d, 1H).

EXAMPLE 43

4,7-Dihydroxy-3-[4-(2-methoxyphenyl)butyl]-2H-1-benzopyran-2-one

The title compound was prepared from 4,7-dihydroxy-2H-1-benzopyran-2-one and 4-(2-methoxyphenyl)butyryl chloride as described in Example 13, m.p. 161°–162° C. NMR (DMSO-$d_6$) δ1.39–1.55 (m, 4 H), 2.44–2.59 (m, 4H), 3.75 (s, 3H), 6.65 (d, 1H), 6.75–7.15 (m, 5H), 7.72 (d, 1H), 10.41 (bs, 1H), 11.05 (bs, 1H).

EXAMPLE 44

4-Hydroxy-3-(3-phenoxypropyl)-2H-1-benzopyran-2-one

The title compound was prepared from the ketoester of Example B and 3-phenoxypropyl bromide following the procedure used in Example 1; m.p. 125°–126° C. NMR (DMSO-$d_6$) δ1.91 (m, 2H), 2.68 (t, 2H), 3.99 (t, 2H), 6.90 (m, 3H), 7.25 (t, 2H), 7.35 (m, 2H), 7.60 (t, 1H), 7.94 (d, 1H), 11.37 (bs, 1H).

4.3 DETERMINATION OF HIV PROTEASE INHIBITION

4.3.1 Starting Materials

DTT Buffer:

1.0 mM dithiothreitol (DTT) was prepared fresh daily in 0.1% polyethylene glycol (mw 8000) 80 mM NaOAc, 160 mM NaCl, 1.0 mM EDTA, and brought to pH 4.7 with HCl.

HIV-1 Protease:

The enzyme is obtained from Bachem Bioscience Inc. The undiluted enzyme is thawed from −80° C. and diluted 50-fold with DTT buffer. The solution is always kept at 0° C. on ice water and used in the experiment within 20 minutes after thawing.

Enzyme Substrate:

Substrate III from Bachem Bioscience Inc. is the undecapeptide H-His-Lys-Ala-Arg-Val-Leu-p-Nitrophenylalanine-Glu-Ala-Norleucine-Ser-NH$_2$(>97% purity). A 200 μM stock solution in DTT buffer is prepared and stored on ice. Substrate solution is prepared fresh daily.

Test Compound:

10 mM inhibitor (I) in dimethyl sulfoxide (DMSO) is diluted to 200 μM with DTT buffer. From the 200 μM stock solution is made a 10 μM stock solution with 2% DMSO in DTT buffer. The two inhibitor solutions are used to make final (I)=100, 50, 20, 10, 5, 0.5 and 0 μM with 2% DMSO in DTT buffer in each reaction well (total inhibitor volume of 50 μl).

4.3.2 Assay

To each reaction well is added 20 μl of substrate (final concentration of 40 μM), 50 μl of inhibitor (at a concentration such that final dilution will produce the test concentration) and 20 μl of DTT buffer. The reaction plate (96 wells) is incubated at 37° C. for at least 5 minutes.

10 μl of the diluted protease is added to the reaction well while the reaction plate is shaking. Once shaken for 10 seconds, the plate is returned to the heating block at 37° C. (Final reaction volume= 100 μl)

The reaction is incubated for 5 minutes at 37° C. The reaction is stopped by placing the reaction plate on the shaker and adding 20 μl of 10% trifluoroacetic acid (TFA) and shaking for 10 seconds. The amount of proteolysis is then determined by separation of noncleaved substrate and two cleaved products with reverse-phase HPLC, while measuring absorbance at 220 nm to determine the relative peak areas of the three components. The relative peak areas are used to calculate % conversion to product as a function of inhibitor concentration. The data is plotted as % Control (the ratio of % conversion in the presence and absence of inhibitor×100) versus inhibitor concentration and fit with the equation $Y= 100/1+(X/IC_{50})^A$, where $IC_{50}$ is the inhibitor concentration at 50% inhibition and A is the slope of the inhibition curve.

The results of this assay are displayed in Table 1.

TABLE 1

| | HIV Protease Inhibition Results |
|---|---|
| Example # | 50% Inhibition Concentration [μM] |
| 4 | 1.9 |
| 7 | 1.3 |
| 8 | 0.5 |
| 9 | 5.0 |
| 10 | 1.2 |
| 13 | 1.7 |
| 14 | 2.8 |
| 22 | 1.4 |
| 23 | 5.0 |
| 37 | 0.6 |
| 42 | 0.4 |
| 43 | 0.5 |

Anti-HIV-1 Activity in Cells

Using the general methods of Pauwels et al., (*J. Virol. Methods*, 16: 171–185 (1987) and Mann et al. (*AIDS Research and Human Retroviruses*, 253–255 (1989)) antiviral assays of acute HIV-1 infection were performed in the H9 cell line. Cultures were batch infected in 1 ml of RPM1 1640 media/10% fetal calf serum containing $10^7$ cells and $10^5$ infectious doses of HIV-1$_{iiib}$ for an effective multiplicity of infection of 0.01. After 2 hours of viral absorption, cells were washed once and plated in 96-well microtiter plates at a density of $10^4$ cells per well. Test compounds were added to produce the desired concentration of drug and 0.2% DMSO in a final volume of 200 μl. Uninfected parallel cultures were maintained for XTT cytotoxicity assay at 7 days post infection. Cultures were tested for viral replication by reverse transcriptase assay at 4 and 7 days post infection.

| Antiviral Activity in H9 Cells | |
|---|---|
| Example # | Therapeutic Concentration for 50% Protection of Cells [μM] |
| 8 | 58 |
| 13 | 13 |

It should be apparent to those skilled in the art that other compositions not specifically disclosed in the instant specification are, nevertheless, contemplated thereby. Such other compositions are considered to be within the scope and spirit of the present invention. Hence, the invention should not be limited by the description of the specific embodiments disclosed herein but only by the following claims.

What is claimed is:

1. A compound or a pharmaceutically acceptable salt thereof of formula

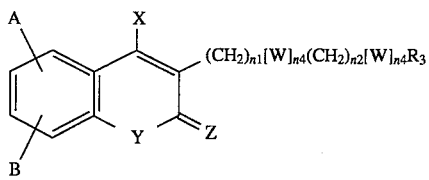

wherein

X is $OR_1$ or SH wherein $R_1$ is hydrogen or $COR_2$ wherein $R_2$ is a straight or branched alkyl chain containing 1 to 5 carbon atoms, a cyclic alkyl containing 3 to 6 carbon atoms, or a hydrogen atom;

Z is oxygen or sulfur;

Y is oxygen;

W is oxygen, $NR_3$, $C(R_3)_2$, $NCOV_{n4}R_3$, $NR_3COV_{n4}$, CO, CH=CH, $S(O)_{n3}$, C≡C, $CNOR4$, or $CR_3OR_3$ wherein V is oxygen, sulfur, $NR_3$, or $CHR_3$; $R_3$ is $(CH_2)_{n3}Ar$ wherein Ar is phenyl, naphthyl, or a substituted derivative thereof wherein the substituents are one or more of F, Cl, Br, $OR_4$, $N(R_4)_2$, $NO_2$, $CO_2R_4$, $CON(R_4)_2$, $COR_4$, $R_4$, $OCH_2O$, $OCH_2CH_2O$, or CN; $R_4$ is hydrogen, a straight or branched alkyl group consisting of 1 to 5 carbon atoms, a cycloalkyl consisting of 3 to 6 carbon atoms, or a substituted derivative thereof wherein the substituents are one or more of $CO_2R_2$, $CON(R_2)_2$, F, $OR_2$, phenyl, naphthyl, or $CF_3$;

n1, n2, n3, and n4 are integers of from 0 to 4, 0 to 4, 0 to 2, and 0 to 1, respectively, with the proviso that n2 is zero when intra-chain n4 is zero, and with the further proviso that n2 is of from two to four when two intra-chain groups W are heteroatoms; and A and B are independently F, Cl, Br, $OR_4$, $N(R_4)_2$, $NO_2$, $CO_2R_4$, $CON(R_4)_2$, $COR_4$, $R_4$, $OCH_2O$, $OCH_2CH_2O$, or CN.

2. A compound of the formula of claim 1 wherein

X is $OR_1$ wherein $R_1$ is H or $COR_2$ wherein $R_2$ is methyl, ethyl, isopropyl, or isobutyl;

Z is oxygen;

Y is oxygen;

W is O, $NR_3$, $C(R_3)_2$, CH=CH, or S wherein $R_3$ is $(CH_2)_{n3}Ar$ wherein Ar is phenyl, or a substituted derivative thereof wherein the substituents are one or more of F, Cl, Br, $OR_4$, $N(R_4)_2$, $CO_2R_4$, $R_4$, $OCH_2O$, or CN wherein $R_4$ is H, $CH_3$, $CH_3CH_2$, phenyl, or a substituted derivative thereof wherein the substituents are one or more of $CF_3$, $CO_2R_2$, $OR_2$, phenyl, or $CON(R_2)_2$;

n1, n2, n3, and n4 are integers of from 0 to 4, 0 to 4, 0 to 3, and zero or one, respectively; and A and B are independently H, Cl, Br, F, I, phenyl, $OR_4$, $R_4$, $CO_2R_4$, $OCH_2O$, or $OCH_2CH_2O$.

3. A compound of the formula of claim 1 wherein

X is hydroxyl;

Z is oxygen;

Y is oxygen;

W is oxygen, sulfur, or $C(R_3)_2$; $R_3$ is $(CH_2)_{n3}Ar$ wherein Ar is phenyl, or a substituted derivative thereof wherein the substituents are one or more of F, Cl, Br, $OR_4$, $CO_2R_4$, $R_4$, or $CO_2H$ wherein $R_4$ is H, methyl, ethyl, phenyl, or cycloalkyl of 3 to 6 carbons, or the substituted derivatives thereof wherein the substituents are one or more of $CF_3$, $CO_2H$, $CO_2CH_3$, $CO_2CH_2CH_3$, OH, CN, or $OCH_3$;

n1, n2, n3, and n4 are integers of from 0 to 4, 0 to 2, 0 to 2, and 0 to 1, respectively; and A and B are independently chlorine, bromine, fluorine, iodine, phenyl, $OCH_3$, $CO_2CH_3$, $CO_2CH_2CH_3$, methyl, ethyl, OH or benzyl.

4. A compound selected from the group consisting of

4-Hydroxy-3-[3-[3-(hydroxymethylphenoxy]propyl]-2H-1-benzopyran-2-one,

4-Hydroxy-3-[2-(phenylmethoxy)ethyl]-2H-1-benzopyran-2-one,

3-[3-(3-Aminophenoxy)propyl]-4-hydroxy-2H-1-benzopyran-2-one,

4-Hydroxy-3-[4-(2-methoxyphenyl)butyl]-2H-1-benzopyran-2-one,

4-Hydroxy-3-[4-(2-hydroxyphenyl)butyl]-2H-1-benzopyran-2-one,

4-Hydroxy-3-[3-(4-methoxyphenoxy)propyl]-2H-1-benzopyran-2-one,

3-[3-(3-Chlorophenoxy)propyl]-4-hydroxy-2H-1-benzopyran-2-one,

4-Hydroxy-7-methoxy-3-[4-(2-methoxyphenyl)butyl]-2H-1-benzopyran-2-one,

4-Hydroxy-3-[3-methyl-1-(2-phenoxyethyl)butyl]2H-1-benzopyran-2-one,

4-Hydroxy-3-(3-phenoxy-4-phenylbutyl)-2H-1-benzopyran-2-one,

4-Hydroxy-3-[2-phenyl-1-[(phenylmethyl)thio]ethyl]-2H-1-benzopyran-2-one,

4-Hydroxy-[3-phenoxy-1-(phenylmethyl)propyl]-2H-1-benzopyran-2-one,

Ethyl 3-[3-(4-hydroxy-2-oxo-2H-1-benzypyran-3-yl)propoxy]benzoate,

3-[3-(3-Cyanophenoxy)propyl]-4-hydroxy-2H-1-benzopyran-2-one, 4,7-Dihydroxy-3-[4-(2-methoxyphenyl)butyl]-2H-1-benzopyran-2-one, and 3-[(Cyclohexylthio)phenylmethyl]-4-hydroxy-2H-1-benzopyran-2-one.

5. A pharmaceutical composition for the treatment of infection or disease caused by a retrovirus, which comprises an amount of the compound of claim 1 sufficient to provide an antivirally effective dosage of the compound in the range of about 1 to about 50 mg/kg-day and a pharmaceutically acceptable carrier.

6. A pharmaceutical composition for the treatment of infection or disease caused by a retrovirus, which comprises the compound of claim 1 sufficient to provide a steady state peak plasma concentration of the compound in the range of about 1–50 μM and a pharmaceutically acceptable carrier.

7. A method of treatment of infection or disease caused by a retrovirus, which comprises administering to a subject in need of such treatment a composition of claim 1.

8. A pharmaceutical composition for the treatment of infection or disease caused by a retrovirus, which comprises an amount of the compound of claim 1 which composition if tested in an in vitro protease inhibition assay is equivalent to 20 percent or greater of the concentration of the compound of claim 1 required to reduce the protease activity by fifty percent and a pharmaceutically acceptable carrier.

\* \* \* \* \*